(12) United States Patent
Fouche et al.

(10) Patent No.: US 9,061,023 B2
(45) Date of Patent: Jun. 23, 2015

(54) MANAGEMENT AND TREATMENT OF BENIGN PROSTATIC HYPERPLASIA

(75) Inventors: Gerda Fouche, Pretoria (ZA); Vinesh Jaichand Maharaj, Pretoria (ZA); Xolani Mthembu, Mahube Valley (ZA); Louis Ackerman, Pretoria (ZA); Marina Van Der Merwe, Pretoria (ZA)

(73) Assignee: CSIR (ZA)

( * ) Notice: Subject to any disclaimer, the term of this patent is extended or adjusted under 35 U.S.C. 154(b) by 586 days.

(21) Appl. No.: 12/734,373

(22) PCT Filed: Apr. 8, 2008

(86) PCT No.: PCT/IB2008/051330
§ 371 (c)(1),
(2), (4) Date: Apr. 26, 2010

(87) PCT Pub. No.: WO2009/053857
PCT Pub. Date: Apr. 30, 2009

(65) Prior Publication Data
US 2010/0316748 A1    Dec. 16, 2010

(30) Foreign Application Priority Data

Oct. 26, 2007  (ZA) ..................... 07/9260

(51) Int. Cl.
*A61K 36/00* (2006.01)
*A61K 36/48* (2006.01)

(52) U.S. Cl.
CPC ...................... *A61K 36/48* (2013.01)

(58) Field of Classification Search
None
See application file for complete search history.

(56) References Cited

U.S. PATENT DOCUMENTS

2005/0136132 A1*  6/2005  Liu et al. ................. 424/725

FOREIGN PATENT DOCUMENTS

WO    WO 2006/013420    2/2006

OTHER PUBLICATIONS

Baderschneider et al, Isolation and characterization of novel benzoates, cinnamates, flavonoids and lignans from Riesling wine and screening for antioxidant activity, J. Agric Food Chem 2001, 49, 2788-2798.*
Aaku et al, Chemical and antimicrobial studies on *Elephantorrhiza elephantina*, Fitoterapia LXIX (5): 464-465, 1998.*
Liao S.; "The Medicinal Action of Androgens and Green Tea Epigallocatechin Gallate"; Hong Kong Medical Journal; Dec. 1, 2001; p. 369-374; vol. 7, No. 4; HK.
Hiipakka R A et al.; "Structure-activity relationships for inhibition of human 5[alpha]-reductases by polyphenols"; Biochemical Pharmacology; Mar. 15, 2002; p. 1165-1176; vol. 63, No. 6; US.
Wanjala C C et al.; "A new stilbene glycoside from *Elephantorrhiza goetzei*"; Fitoterapia; Aug. 2001; p. 649-655; vol. 72, No. 6.
Moyo Fortune et al.; "A new flavan from *Elephantorrhiza goetzei*"; Fitoterapia; Aug. 1999; p. 412-416; vol. 70, No. 4.
Bisson J-F et al.; "Preventive effects of Acticoa powder, a cocoa polyphenolic extract, on experimentally induced prostate hyperplasia in Wistar-Unilever rats"; Journal of Medicinal Food; Dec. 12, 2007; p. 622-627; vol. 10, No. 4; Mary Ann Lievert, Larchmont, NY, US.
Viljoen et al., The composition, geographical variation and antimicrobal activity of *Lippia javanica* (Verbenaceae) leaf essential oils, Journal of Ethnopharmacology (2005) 96:271-277.
Bagdonaite et al., Variation in concentrations of major bioactive compounds in *Hypericum perforatum*, Industrial Crops and Products (2012) 35:302-308.
Bjorkman et al., Phytochemicais of *Brassicaceae* in plant protection and human health-Influences of climate, environment and agronomic practice, Phytochemistiy (2011) 72:538-556.

* cited by examiner

*Primary Examiner* — Qiuwen Mi
(74) *Attorney, Agent, or Firm* — Kramer Levin Naftalis & Frankel LLP

(57) ABSTRACT

The invention provides the use of an extract of a plant of the genus *Elephantorrhiza* and at least one compound selected from quercitin-3'-O-glucoside, trans-3-O-galloyl-3,3',5,5',7-pentahydroxyflavan, taxifolin-3'-O-glucoside, catechin and epicatechin in the preparation of a medicament for the treatment of benign prostatic hyperplasia (BPH). The mode of action is by a route selected from blocking the conversion of testosterone to dihydrotestosterone by inhibiting the 5α-reductase enzyme or by reducing oxidative stress or both.

17 Claims, No Drawings

MANAGEMENT AND TREATMENT OF BENIGN PROSTATIC HYPERPLASIA

This application is a National Phase of PCT Patent Application No. PCT/IB2008/051330 having International filing date of Apr. 8, 2008, which claims the benefit of priority of SOUTH AFRICA Patent Application No. 200709260 filed on Oct. 26, 2007. The contents of the above applications are all incorporated by reference as if fully set forth herein in their entirety.

THIS INVENTION relates to the management and treatment of benign prostatic hyperplasia (BPH).

Benign prostatic hyperplasia (BPH) is a common, significant problem that affects mainly males over the age of 50, although the disease itself might have manifested itself earlier[1]. It affects about 80% of men 70 to 80 years old and is a major public health problem[2]. The main symptoms are the physical enlargement of the prostate gland which, in turn, results in urinary frequency, urgency, nocturia and dribbling or a slow stream. If this condition is not treated, it can lead to urinary tract infections, urinary retention and in rare cases, kidney disease[3].

In BPH, the cells of the prostate undergo changes, the microscopic foci grow to form macroscopic nodules and these then displace normal prostatic tissue which results in urethra compression. The compression itself results in either physical enlargement of the prostate or contraction of the prostate and urethral smooth muscles in response to nerve stimulation. BPH prevalence has a serious impact on the quality of life of older males. Over the years, scientific research has been undertaken in an attempt to study the mechanism of action and pathogenesis of BPH to help treat sufferers. The origin of the causes of this disease remains unresolved and many different hypotheses have been reported to date[4]. However, hormonal and histological changes within men over 50 years are considered to be the major contributing factors[5]. The main causes of BPH appear to be androgenic hormones and oxidative stress.

Androgenic Hormones

In the human prostate, androgens are responsible for the normal growth, cell differentiation and maintaining the maturing of the gland. As men grow older, the function of androgen continues and this could lead to risk factors and susceptibility against diseases such as prostate cancer[6]. The conversion of the androgenic hormone, testosterone to dihydrotestosterone (DHT) that is regulated by the steroid 5α-reductase enzyme (Scheme 1) seems to be one of the causative factors for benign prostatic hyperplasia[7]. It is believed that the higher conversion of testosterone to dihydrotestosterone contributes to the pathogenesis of BPH. Steroid 5α-reductase has two different iso-forms, i.e. type 1 (5α-R1) and type 2 (5α-R2)[8]. These two types are characterized in humans, monkeys, rats and mice and are expressed by different genes. Type 1 is mainly responsible for androgen metabolism, whereas type 2 plays a role in prostate cancer. It is also believed that the same enzyme is responsible for male baldness, acne, hirsutism and BPH.

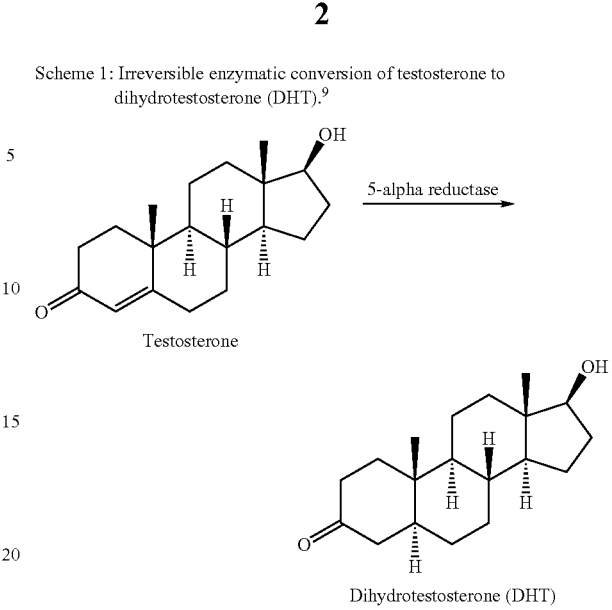

Scheme 1: Irreversible enzymatic conversion of testosterone to dihydrotestosterone (DHT).[9]

This reaction occurs within the prostate, after DHT is formed, it is further metabolized into 3α- and 5α-diols, which are water soluble and inactive as androgens and cannot re-form DHT.

Oxidative Stress

Numerous investigations have shown that lipid peroxides and reactive oxygen species (ROS) (e.g. superoxide radicals, singlet oxygen, hydrogen peroxide, hydroxyl radicals) are involved in the regulation of cellular proliferation and in the aetiology of a variety of diseases, including accelerated aging and prostate cancer. Intracellular ROS are generated spontaneously as a result of oxygen interaction with reducing compounds, or as intermediates of some metabolic reactions. Under normal conditions, the ROS level in the tissue is controlled by antioxidants and antioxidant enzymes such as glutathione, vitamin C, vitamin E, superoxide dismutase, catalase, glutathione reductase, etc. The augmentation of ROS concentration (oxidative stress) is commonly associated with increasing age and with several diseases accompanied by tissue inflammation. Ripple et al. demonstrated that the oxidative stress is also increased by androgen treatment in androgen responsive human prostate carcinoma cells LNCaP[10]. It is proposed that redox alteration may play a key role in a signal transduction pathway important for regulation cell growth[11].

BPH has been treated with 5α-reductase inhibitors and with antioxidants.

5α-Reductase Inhibitors

The prevalence of BPH has led to the discovery of the chemopreventive drugs which are presently marketed. The introduction of these drugs led to a decline in usage of surgical methods. The two types of prescribed drugs are α-blockers and 5α-reductase inhibitors. α-Blockers help to relax the smooth muscle in the prostate which constrict the urethra and bladder neck. They tend to be non-specific and include doxazosin (Cardura®), prozosin (Minipress®), tamsulosin (Flomax®) and terazosin (Hytrin®)[20]. These types of drugs are used worldwide as they offer quick relief, no adverse effect on erectile or urinary function, can be used with any size of the prostate and are less expensive. Although these drugs are used, they have shown considerable side effects such as hypotension, dizziness, upper respiratory symptoms, headache, fatigue and sexual disturbances[12].

The enzyme inhibitors (5α-reductase inhibitors) offer much more relevant effects as they block the conversion of testosterone to dihydrotestosterone which then results in reduction in prostate sizes by approximately 25%. The only enzyme inhibitor available so far is a Merck product, finasteride (Proscar®). Its main advantages are its ability to lower the DHT level by 70% to 80% and improve urinary flow rate (15% to 20%), while causing no cardiovascular side effects and hence reducing the need for prostate surgery. This drug is not very effective in men with smaller prostates as it may cause reduction in erection rate by up to 8%, a reduction in sex drive by 6% and a reduction in semen volume by 4%.

Antioxidants

A sizable body of evidence that plant antioxidants play an important role in biological systems as agents of anti-oxidative defence has been published[13]. The ameliorative effect of cactus flower extract on prostate hyperplasia includes not only the inhibition the prostatic 5α-reductase and aromatase activity but also the regulation of free radical processes as it is a strong antioxidant. The full significance of cactus flower extracts in the treatment of BPH is being evaluated in clinical trials[14]. Other dietary treatments include green tea and saw palmento[15].

The present invention shows that extracts and compounds isolated from extracts of plants of the genus *Elephantorrhiza* can be used in the treatment of BPH. The plants of the Fabaceae family include the genus *Elephantorrhiza*. This genus includes the species *Elephantorrhiza elephantina* and *Elephantorrhiza goetzei*. Its vernacular names are eland's bean, elandswortel, elandsboontjie and intolwane[16]. *Elephantorrhiza elephantina* is widely distributed in southern African countries such as Mozambique, Lesotho, South Africa, Swaziland, Zimbabwe, Botswana and Namibia[17].

The extracts have been found to contain gallic acid (1), its methyl ester (2), quercitin-3'-O-glucoside (3), trans-3-O-galloyl-3,3',5,5',7-pentahydroxyflavan (4), taxifolin-3'-O-glucoside (5), (+)-catechin (6a) and (−)-epicatechin (6b). The structures of these compounds are set out below.

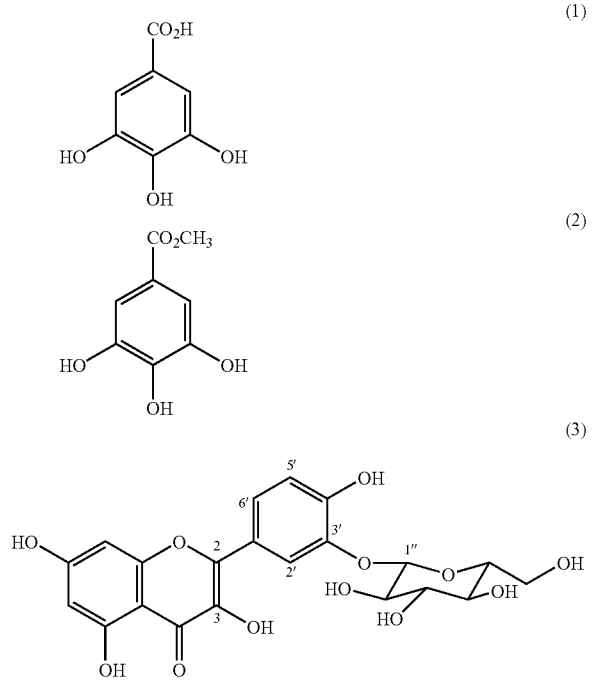

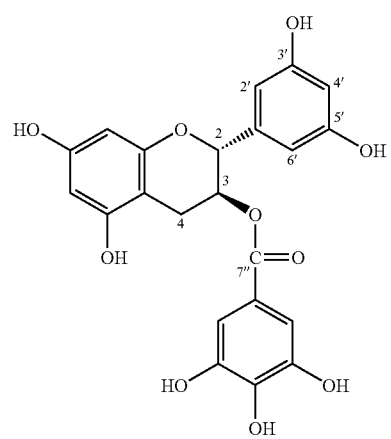

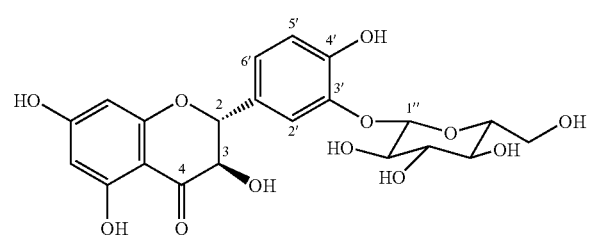

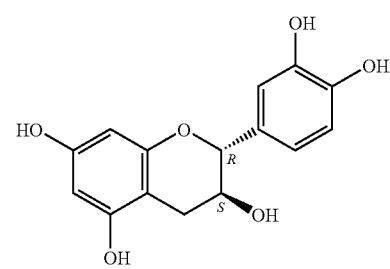

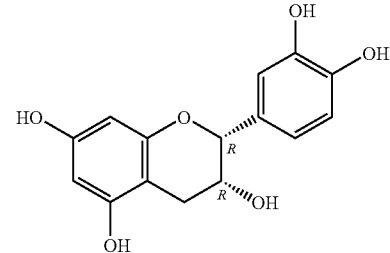

According to a first aspect of the invention, there is provided the use of an extract of a plant of the genus *Elephantorrhiza* and at least one compound selected from quercitin-3'-O-glucoside, trans-3-O-galloyl-3,3',5,5',7-pentahydroxyflavan, taxifolin-3'-O-glucoside, catechin and epicatechin in the preparation of a medicament for the treatment of benign prostatic hyperplasia (BPH) by a route selected from one or both of blocking the conversion of testosterone to dihydrotestosterone by inhibiting the 5α-reductase enzyme and reducing oxidative stress.

The extracts may be aqueous extracts. The extracts may, for example, be prepared by washing the rhizomes of the plant, chopping the washed rhizomes into small pieces and drying the chopped material in an oven at 60° C. The oven-dried plant material may then be ground and boiled in distilled water for about an hour. The resulting filtrate (or tea) may be cooled and decanted and separated from the plant material, filtered successively through a cheese cloth and then through filter paper. The resultant extract may be spray-dried to produce a solid powdered extract. The extract may instead be freeze-dried to give a dry extract. The composition may include each of the compounds. The catechin and epicatechin may be present as an approximately 1:1 ratio of the isomers.

According to a second aspect of the invention, there is provided the use of an extract of a plant of the genus *Elephantorrhiza* in the preparation of a medicament for the treatment of benign prostatic hyperplasia (BPH) by a route selected from one or both of blocking the conversion of testosterone to dihydrotestosterone by inhibiting the 5α-reductase enzyme and reducing oxidative stress.

The plant may be a plant of the species *E. elephantina* or *E. goetzei*.

According to a third aspect of the invention, there is provided the use of a composition comprising a mixture of two or more compounds selected from quercitin-3'-O-glucoside, trans-3-O-galloyl-3,3',5,5',7-pentahydroxyflavan, taxifolin-3'-O-glucoside, catechin and epicatechin in the preparation of a medicament for the treatment of benign prostatic hyperplasia (BPH) by a route selected from one or both of blocking the conversion of testosterone to dihydrotestosterone by inhibiting the 5α-reductase enzyme and reducing oxidative stress.

The composition may include each of the said compounds. The catechin and epicatechin may be present as a 1:1 ratio of the isomers.

The invention also provides a substance or composition for use in a method of treatment of benign prostatic hyperplasia (BPH), the substance or composition comprising an extract of a plant of the genus *Elephantorrhiza* and the method including the step of administering the substance or composition to a human in need of treatment.

The invention further provides a substance or composition for use in blocking the conversion of testosterone to dihydrotestosterone by inhibiting the 5α-reductase enzyme, the substance or composition comprising an extract of a plant of the genus *Elephantorrhiza* and the method including the step of administering the substance or composition to a human in need of treatment.

The invention further provides a substance or composition for use in the management of benign prostatic hyperplasia (BPH) by reducing oxidative stress, the substance or composition comprising an extract of a plant of the genus *Elephantorrhiza* and the method including the step of administering the substance or composition to a human in need of treatment.

The plant may be a plant of the species *E. elephantina* or *E. goetzei*.

The invention further provides a substance or composition for use in a method of treatment of benign prostatic hyperplasia (BPH), the substance or composition comprising a mixture of compounds selected from quercitin-3'-O-glucoside, trans-3-O-galloyl-3,3',5,5',7-pentahydroxyflavan, taxifolin-3'-O-glucoside, catechin and epicatechin and the method including the step of administering the substance or composition to a human in need of treatment.

The invention further provides a substance or composition for use in a method of blocking the conversion of testosterone to dihydrotestosterone by inhibiting the 5α-reductase enzyme, the substance or composition comprising a mixture of compounds selected from quercitin-3'-O-glucoside, trans-3-O-galloyl-3,3',5,5',7-pentahydroxyflavan, taxifolin-3'-O-glucoside, catechin and epicatechin and the method including the step of administering the substance or composition to a human in need of treatment.

The invention further provides a substance or composition for use in a method of managing benign prostatic hyperplasia (BPH) by reducing oxidative stress, the substance or composition comprising a mixture of compounds selected from quercitin-3'-O-glucoside, trans-3-O-galloyl-3,3',5,5',7-pentahydroxyflavan, taxifolin-3'-β-glucoside, catechin and epicatechin and the method including the step of administering the substance or composition to a human in need of treatment.

The crude spray-dried extract may be purified by a modified counter-current partitioning method. For example, the solid spray-dried extract may be partitioned against (i) water/isobutanol/hexane, (ii) n-butanol to produce four different fractions which can be coded BP-5-11A (isobutanol), BP-5-11B (n-butanol), BP-5-11C (water) and a hexane fraction.

In an embodiment of the invention, the isobutanol fraction was purified using flash silica chromatography to afford 13 fractions. Some of these fractions were combined based on their TLC profile and further purified using flash silica. Selected fractions were further fractionated using Sephadex LH-20 and additional flash silica chromatography to afford gallic acid (1), its methyl ester (2), quercitin-3'-O-glucoside (3), trans-3-O-galloyl-3,3',5,5',7-pentahydroxyflavan (4), taxifolin-3'-O-glucoside (5), (+)-catechin (6a) and (−)-epicatechin (6b).

In vitro biological assays of the extracts, compounds and mixtures of compounds were undertaken to determine their inhibition of the enzyme 5α-reductase. The efficacy of each isolated compound as well as the crude spray-dried extract was expressed as percentage inhibitory activity and these compounds were tested at different concentrations.

A mixture of the four isolated flavonoids (3), (4), (5), (6a) and (6b) was prepared (Table 1) and the mixture tested at three different concentrations (100, 10 and 1 μg/mL). Gallic acid (1) and its methyl ester (2) were reported to be ineffective when tested against the steroid 5α-reductase enzyme except when it was structurally attached to a catechin molecule[18] and were not tested.

TABLE 1

Preparation of the mixture

| Compound name | Compound number | Mass percentage ratio (%) |
|---|---|---|
| Quercetin 3'-O-glucoside | (3) | 25 |
| Trans-3-O-galloyl-3,3',5,5',7-pentahydroxyflavan | (4) | 25 |
| Taxifolin 3'-O-glucoside | (5) | 25 |
| Catechin and epicatechin mixture (1:1 ratio) | (6a) and (6b) | 25 |

The inhibitory effect of the crude extract, the isolated compounds and a mixture of the compounds on the steroid 5α-reductase was investigated and the results are given in Table 2.

TABLE 2

In vitro inhibition of steroid 5α-reductase enzyme by the crude extract, isolated compounds and a mixture thereof.

| Compound number | Test concentration | % inhibition |
|---|---|---|
| Spray-dried crude extract SM010119B | 100 | 92 |
| Compound (3) | 1 Mm | −9 |
| Compound (4) | 1 μM | −2 |
| Compound (5) | 1 μM | 3 |
| Compound (6a) and (6b) (mixture) | 1 μM | −6 |

TABLE 2-continued

In vitro inhibition of steroid 5α-reductase enzyme by the crude extract, isolated compounds and a mixture thereof.

| Compound number | Test concentration | % inhibition |
|---|---|---|
| Mixture of (3), (4), (5), (6a) and (6b) | 100 µg/mL | 80 |
| Finasteride* | 0.025 µM | 50 |

*Reference compound
Inhibition >50% is regarded as significant

The crude spray-dried extract and the mixture of compounds showed significant inhibition of the steroid 5α-reductase enzyme when tested at 100 µg/mL, these gave 92% and 80% inhibition respectively. It is evident from Table 2 that the individual isolated compounds did not exhibit any significant activity when tested at 1 µM compared to the test compound finasteride which gave an $IC_{50}$ of 0.025 µM. These results demonstrate that the product acts as a mixture for the treatment of BPH through the inhibition of steroid 5α-reductase enzyme.

The antioxidant assay was based on the DPPH assay. DPPH is a radical and when a compound with radical scavenging properties reacts with DPPH, the purple colour disappears and a yellow colour is observed. The decolourisation of a purple colour to a yellow colour is measured by a chromameter. The intensity of the yellow colour gives an indication of antioxidant activity. The compounds (3), (4), (6a) and (6b) were tested and showed different levels of activities against DPPH, see Table 3. The antioxidant activity was expressed as percentage radical scavenging capacity (RSC). The crude spray-dried extract was tested at five (5) dose concentrations namely 100, 50, 25, 12.5 and 6.25 ppm and showed very good radical scavenging capacity (potent antioxidant), equivalent to green tea extract.

At 6.25 ppm, the RSC was 82%. The epigallocatechin standard gave a 61% RSC at 1 ppm. Green tea was also tested at the same concentrations as *E. elephantina* and gave a RSC of 41% at 6.25 ppm. This result showed that *E. elephantina* extract exhibited better antioxidant activity than green tea at the same test concentration. Isolated compounds showed good decolourisation of DPPH and were classified as moderate. Green tea was also tested at 20 ppm and gave a RSC of 68% whereas *E. elephantina* extract when tested at 12.5 ppm gave a RSC value of 95%. These results confirm that *E. elephantina* extract has a better antioxidant activity than green tea.

TABLE 3

Shows antioxidant activity of spray dried extract of *E. elephantina* extract, compounds (3), (4), (6a) and (6b), green tea and epigallocatechin gallate standard

| Compound | Concentration (ppm) | % RSC |
|---|---|---|
| Spray dried extract of *E. elephantina* | 100 | 95 |
| | 50 | 95 |
| | 25 | 95 |
| | 12.5 | 95 |
| | 6.25 | 82 |
| Compound (3) | 100 | 95 |
| | 50 | 95 |
| | 25 | 95 |
| | 12.5 | 77 |
| | 6.25 | 41 |
| Compound (5) | 100 | 21 |
| | 50 | 13 |
| | 25 | 10 |
| | 12.5 | 8 |
| | 6.25 | 10 |
| Compound (6a) and (6b) | 100 | 94 |
| | 50 | 94 |
| | 25 | 86 |
| | 12.5 | 48 |
| | 6.25 | 28 |
| Green tea | 100 | 96 |
| | 50 | 96 |
| | 25 | 96 |
| | 12.5 | 71 |
| | 6.25 | 41 |
| Epigallocatechin gallate | 100 | 95 |
| | 10 | 95 |
| | 1 | 61 |
| | 0.1 | 8 |
| | 0.01 | 8 |

According to a fourth aspect of the invention, there is provided the compound trans-3-O-galloyl-3,3',5,5',7-pentahydroxyflavan.

According to a fifth aspect of the invention, there is provided the use of trans-3-O-galloyl-3,3',5,5',7-pentahydroxyflavan in the preparation of a medicament for use in the treatment of benign prostatic hyperplasia (BPH) by a route selected from one or both of blocking the conversion of testosterone to dihydrotestosterone by inhibiting the 5α-reductase enzyme and reducing oxidative stress.

The invention is now described, by way of example, with reference to the following non-limiting Example.

EXAMPLE 1

Preparation and Fractionation of the Extract

Bulk rhizomes of *E. elephantina* were sliced and dried overnight in an oven at 60° C. to produce 5 kg of oven dried plant material. The oven-dried material was then ground and boiled in 25 l of distilled water for 1 hour. The filtrate (tea) was cooled and decanted and separated from the plant material, filtered through a cheese cloth first and then through Whatman No. 1 filter paper. The resultant extract was then spray-dried on a large scale and 50 g solid extract was recovered. Of this, 23 g was utilized for the fractionation process. A modified counter-current partitioning method was employed to purify the crude extract. This method entailed partitioning against (i) water/isobutanol/hexane, (ii) n-butanol. Four different fractions were obtained and coded BP-5-11A (isobutanol), BP-5-11B (n-butanol), BP-5-11C (water) and a hexane fraction. The isobutanol fraction was purified using flash silica chromatography, (mobile phase $CHCl_3$/MeOH, 90:10) and afforded 13 fractions coded as BP-5-12 A-M. Some of these fractions were combined based on their TLC profile while fraction BP-5-12A (573 mg) was further purified using flash silica (2% MeOH/$CHCl_3$) to yield 13 fractions which were coded BP-5-16 A to M. BP-5-16A, 16B, 16C and 16D were combined and further purified using flash silica to yield pure gallic acid (1).

Fraction 16H (199 mg) was further fractionated using Sephadex LH-20, 100% EtOH and afforded six fractions (BP-5-20 A to F). Fraction BP-5-20F (65 mg) was purified using flash silica gel and afforded four pure compounds, (2), (3), (4) and (5) and a mixture of two structurally related compounds ((+)-catechin and (−)-epicatechin) (6a) and (6b).

Compound (1)

| | |
|---|---|
| Systematic name: | 3,4,5-Trihydroxybenzoic acid |
| Alternative name: | Gallic acid |
| Yield: | 60 mg |
| Physical description: | Yellowish white crystals |
| Mass spectrum: | MS (ES+) m/z: 171 [M + H]+, $C_7H_6O_5$ |
| UV maxima: | 210, 270 nm |
| Melting point: | 249-250° C., Lit[19] 256-258° C. |

Compound (2)

| | |
|---|---|
| Systematic name: | 3,4,5-Trihydroxybenzoic acid methyl ester |
| Alternative name: | Methyl gallate |
| Yield: | 15 mg |
| Physical description: | Yellowish white crystals |
| Mass spectrum: | MS m/z: 184 [M]+ $C_8H_8O_5$ |
| UV maxima: | 210, 250, 270, 300, 340 nm |
| Melting point: | 202-205° C., Lit[20] 198-200° C. |

Compound (3)

| | |
|---|---|
| Systematic name: | 3,5,7-Trihydroxy-2-[4-hydroxy-3-(3,4,5-trihydroxy-6-hydroxymethyltetrahydropyran-2-yloxy)-phenyl]-chromen-4-one |
| Alternative name: | Quercetin 3'-glucoside |
| Yield: | 58 mg |
| Physical description: | White powder |
| Mass spectrum: | MS(ES+) m/z: 465 [M + H]+, fragment peak m/z 307 loss of sugar moiety, m/z 447 [M − OH]+ $C_{21}H_{20}O_{12}$ |
| Optical rotation: | $[\alpha]_D^{20}$ −40 (c = 0.2 in MeOH) <br> Lit[21]: $[\alpha]_D^{20}$ −63.5 (c = 0.33 g/100 mL in MeOH) |
| Melting point: | 239-241° C., Lit[22] 240-241° C. |
| UV maxima: | 255, 350 nm |

Compound (4)

| | |
|---|---|
| Systematic name: | 3,4,5-Trihydroxybenzoic acid 2-(3,5-dihydroxy-phenyl)-5,7-dihydroxy-chroman-3-yl ester |
| Alternative name: | 3-O-Galloyl-3,3',5',5,7-pentahydroxyflavone |
| Yield: | 9 mg |
| Physical description: | White-yellow crystals |
| Mass spectrum: | HR/MS m/z 442.2120, $C_{22}H_{18}O_{10}$ <br> MS (ESI+) m/z: 443 [M + H]+ |
| Optical rotation: | $[\alpha]_D^{20}$ −49 (c = 0.2 in MeOH) |
| Melting point: | 211-212° C. |
| 1H NMR: | See Table 5.5 (CD3OD) |
| 13C NMR: | See Table 5.5 (CD3OD) |

TABLE 4

13C and 1H NMR (400 MHz, CD3OD) data for compound (4)

| Carbon number | $\delta_c$ Compound (4) | $\delta_H$ (J in Hz) Compound (4) | HMBC, Compound (4) |
|---|---|---|---|
| 2 | 79.5 | 5.06, d, J = 6 | H-2',4,6' |
| 3 | 71.3 | 5.37, q, J = 5.5 | H-4,7",10 |
| 4 | 24.5 | 2.83, dd, J = 16.5, 4.7 <br> 2.71, dd, J = 16.5, 6.1 | H-2,9 |
| 5 | 158.8 | | H-4 |
| 6 | 96.7 | 5.96, d, J = 2.3 | H-8 |
| 7 | 158.3 | | |
| 8 | 95.8 | 5.95, d, J = 2.3 | H-6 |
| 9 | 156.6 | | H-2 |
| 10 | 99.8 | | H-3,7,8 |
| 1' | 131.7 | | H-3 |
| 2' | 114.6 | 6.72, d, J = 1.0 | H-2,4',6' |
| 3' | 146.5 | | |
| 4' | 116.4 | 6.84, s | H-2,2',6' |
| 5' | 146.5 | | |
| 6' | 119.4 | 6.72, s, J = 1.0 | H-2,2',4' |
| 1" | 121.5 | | |
| 2", 6" | 110.3 | 6.97, s | |
| 3", 5" | 140.0 | | |
| 4" | 146.5 | | H-2",6" |
| 7" | 167.7 | | H-2",3,6" |

Compound (5)

| | |
|---|---|
| Systematic name: | (2R,3R)-,2-[3-(β-D-glucopyranosyloxy)-4-hydroxy-phenyl]-2,3-dihydro-3,5,7-trihydroxy-,4H-1-benzo-pyran-4-one |
| Alternative names: | 3,3',4',5,7-Pentahydroxyflavanone 3'-O-glucoside <br> Taxifolin 3'-O-glucoside |
| Yield: | 38 mg |
| Physical description: | Fine orange needles |
| Mass spectrum: | HRMS m/z 466.111, $C_{21}H_{22}O_{12}$ <br> MS (ESI−) m/z: 465 [M − H]− |
| Optical rotation: | $[\alpha]_D^{20}$ −26 (c = 0.2 in MeOH), Lit[23]. $[\alpha]_D^{21}$ −26 c = 0.3 in MeOH) |
| UV maxima: | 290, 327 nm |
| Melting point: | 185-187° C., Lit[24] 203-295° C. |

Compound (6a)

| | |
|---|---|
| Systematic name: | (+)-Catechin |
| Yield: | 43 mg |
| Physical description: | Yellow crystals |
| Mass spectrum: | MS (ESI−) m/z: 289.01 [M − H]− $C_{15}H_{14}O_6$ |

Compound (6b)

| | |
|---|---|
| Systematic name: | (−)-Epicatechin |
| Yield: | 43 mg |
| Physical description: | Yellow crystals |
| Mass spectrum: | MS (ESI−) m/z: 289.01 [M − H]− $C_{15}H_{14}O_6$ |

Bioassays
In Vitro Steroid 5α-Reductase Assay
This work was performed at the MDS Pharma Services, Pharmacology Laboratories, Taiwan. The assay was an in vitro evaluation of the ability of an extract or a pure compound to inhibit the steroid 5α-reductase enzyme from metabolizing testosterone into dihydrotestosterone. This is an enzyme-immunoassay (EIA) for quantitative determination of testosterone in human serum or plasma. The significance of this type of inhibition is that it can lead to eradication of benign prostatic hyperplasia (BPH). Two distinct isozymes are found in mice, rats, monkeys and humans: type 1 and II. Each of these isozymes is differentially expressed in tissues and developmental stages. In human, type 1 steroid 5α-reductase is predominant in the sebaceous glands of most regions of skin, including scalp and liver and is responsible for approximately one third of circulating DHT. Inhibitors of steroid 5α-reductase may be of benefit in the treatment of androgenetic alopecia. This is a specific binding assay whereby the biochemical assay results were expressed as percentage inhibition. Finasteride was used as a reference compound in all experiments.

The method employed was adapted from the scientific literature to maximize reliability and reproducibility[25]. The steroid 5α-reductase enzyme was isolated from the liver of Wistar rats. The test compound was incubated with 20 μg/mL of steroid 5α-reductase preparation which contains 1 μM testosterone and 50 μM NADPH in DTT buffer, pH 6.5 for 30 minutes at 37° C. The reaction was stopped by addition of 1N HCl and neutralized by 1N NaOH and testosterone was quantified using a testosterone EIA Kit. Compounds were screened at 10 μM.

Reference Compound Data

| Compound | IC$_{50}$ (μM) |
|---|---|
| *Finasteride | 0.025 |
| γ-Linolenic acid | 14 |

*refers to the reference compound used.

Antioxidant Screen

This evaluation was carried out at the CSIR, Biosciences, Bioprospecting Platform. The 1,1-diphenyl-2-picrylhydrazyl (DPPH) assay was used to investigate the scavenging properties of extracts and pure compounds. Basically, a DPPH radical is scavenged by the potential antioxidant by donating a proton, forming a reduced DPPH and this resulted in a colour change from purple to yellow. This is quantified by the decrease of absorbance at wavelength 515 nm in the spectrophotometer.

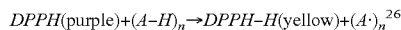

$DPPH(\text{purple}) + (A-H)_n \rightarrow DPPH-H(\text{yellow}) + (A\cdot)_n$ [26]

Since this was a colorimetric test, the appearance of the yellow colour was measured using a chromameter. The final appearance of a more intense yellow colour was used as a good indication of a radical scavenging ability of the extract or compound and this is directly proportional to its antioxidant activity. The antioxidant activity was directly related to the total amount of phenolics and flavonoids present in that particular extract. This method was sensitive enough to indicate and monitor the presence of phenolic-type compounds.

Dilutions of crude extracts were prepared at a single dose (100 ppm) concentration and spotted on a TLC silica gel layers in a form of a dot-blot test, layers were then stained with 2,2-diphenyl-1-picrylhydrazyl radical. Spots with good radical scavenging properties turned yellow and the intensity was measured by a chromameter[5]. The active crude extract or compound was then serially diluted at a five dose concentration, i.e. 100, 50, 25, 12.5 and 6.25 ppm to determine their percentage radical scavenging capacity (% RSC). The activity of the compound or extract was measured against the reference compound, epigallocatechin gallate.

The invention thus provides extracts of *E. elephantina* and mixtures of compounds (3), (4), (5), (6a) and (6b) for the treatment of BPH. More particularly, the invention provides extracts of *E. elephantina* for the treatment of BPH by inhibition of 5α-reductase enzyme, thereby blocking the conversion of testosterone to dihydrotestosterone. It also provides extracts of *E. elephantina* containing compounds (3), (4), (5), (6a) and (6b) for the treatment of BPH by the inhibition of 5α-reductase enzyme thereby blocking the conversion of testosterone to dihydrotestosterone. The invention further provides extracts of *E. elephantina* for the management of BPH by reducing oxidative stress due to its anti-oxidant properties. In addition, the invention provides extracts of *E. elephantina* containing compounds (3), (4), (5), (6a) and (6b) for the management of BPH by reducing oxidative stress due to its anti-oxidant properties.

REFERENCES

1. P. J. Hieble, *Therap. Strat.*, 2004, 1, 243-248.
2. F. Bravi, C. Bosetti, L. D. Maso, R. Talamini, M. Montella, E. Negri, V. Ramazzotti, S., Franceschi, C. L. Vecchia, *Ad. Urol.*, 2006, 67, 1205-1211.
3. M. K. Brawer, *Urol. Tim.*, 1999, 27, 13-18.
4. M. A. Cabelin, A. E. Te, S. A. Kaplan, *Curr. Opin. Urol.*, 2000, 10, 301-306.
5. V. Mirone, F. Fusco., P. Verze, C. Schulman, F. Debruyne, C. Imbimbo, *Europ. Urol. Suppl.*, 2006, 5, 410-417.
6. R. Ross, L. Bernstein, H. Judd, R. Hanisch, M. Pike, B. Henderson, J. *Natl. Cancer Inst.*, 1986, 76, 45-48.
7. G. F. Verlag, *Phytomedicine*, 1996, 3, 121-128.
8. Y. Jin, T. M. Penning, *Best Pract. Res. Clin. Endocrinol Metab.*, 2001, 15, 79-94.
9. A. W. Partin, D. S. Coffey, *Recent Prog. Horm. Res.*, 1994, 49, 293-331.
10. Ripple M O, Henry W F, Rago R P, Wilding G Pro-oxidant-antioxidant shift induced by androgen treatment of human prostate carcinoma cells. *J Natl Cancer Inst*, 1997, 89, 40
11. Burdon R H, Gill V (1993) Cellularly generated active oxygen species and HeLa cells proliferation. *Free Radic Res Commun*, 1993, 19, 203
12. Y. T. Logan, M. T. Belgeri, *Amer. J. Geriat. Pharm.*, 2005, 3, 103-113.
13. Kehrer J P, Smith C V (1994) Free radicals in biology: source, reactivities and roles in the aetiology of human diseases. In: Balz F (ed) Natural antioxidants in human health and disease. Academic Press, London, p 25
14. Adi Jonas á Gennady Rosenblat á Daniel Krapf, William Bitterman á Ishak Neeman, *Urol Res* 1998, 26, 265-270
15. www.uchospitals.edu/online-library/content, www.umm.edu/prostate/bph.htm, Diet and benign prostatic hyperplasia: Implications for prevention. Urology, Volume 68, Issue 3, Pages 470-476 P. Ranjan, D. Dalela, S. Sankhwar
16. J. M. Watt, M. G. Breyer-Brandwijk, The medicinal and poisonous plants of Southern Africa, 2$^{nd}$ Edition, Edinburgh, 1962, 596-597.
17. I. Hedberg, F. Staugard, Traditional medicine in Botswana. Traditional medicinal plants. Ipelegeng publishers, Gabarone, p. 119-120.
18. R. A. Hiipakka, H-Z. Zhang, W. Dai, S. Liao, *Biochem. Pharm.*, 2002, 63, 1165-1176.
19. A. K. Batta, S. Rangaswami, *Phytochemistry*, 1973, 12, 214-216.

20. G. D. Manners, L. Jurd, *Phytochemistry,* 1979, 18, 1037-1042.
21. A. E. Polovinko, G. P. Yakovlev, *Chem. Nat. Compd.,* 1985, 21, 252-253.
22. H-S. Z. Wagner, *Physiol. Chem.,* 1964, 335, 232-239.
23. L. Y. Foo, J. J. Karchesy, *Phytochemistry,* 1989, 28, 1237-1240.
24. G. Hergert, J. Joceah, *J. Org. Chem.,* 1958, 23, 700-704.
25. T. Liang, M. A. Cascieri, A. H. Cheung, G. F. Reynolds, G. H. Rasmusson, *Endocrinol.,* 1985, 117, 571-579.
26. C. Soler-Rivas, J. C. Espin, H. J. Wichers, *Phytochem. Anal.,* 2000, 11, 330-338.

The invention claimed is:

1. A method for treatment of benign prostatic hyperplasia (BPH) or condition associated therewith, comprising administering to a human in need of treatment, a pharmaceutical composition comprising an effective amount of the compound trans-3-O-galloyol-3,3',5,5',7-pentahydroxyflavan.

2. The method of claim 1, wherein the pharmaceutical composition further comprises a compound selected from quercitin-3'-O-glucoside, taxifolin-3'-O-glucoside, catechin and epicatechin.

3. The method of claim 2, wherein said composition comprises all of trans-3-O-galloyol-3,3',5,5',7-pentahydroxyflavan, quercitin-3'-O-glucoside, taxifolin-3'-O-glucoside, catechin and epicatechin.

4. The method of claim 3, in which the catechin and epicatechin are present, in the composition, as an approximately 1:1 ratio of their isomers.

5. The method of claim 1, wherein the pharmaceutical composition further comprises an extract of a plant of the genus *Elephantorrhiza*.

6. The method of claim 5, in which the plant is a plant of the species, *E. elephantina* or *E. goetzi*.

7. The method of claim 5, in which the extract is an aqueous extract of the rhizomes of the plant.

8. The method of claim 5, in which the extract is a spray-dried or freeze-dried extract.

9. A method for treatment of benign prostatic hyperplasia (BPH) or a condition associated therewith, comprising administering, to a human in need thereof, a plant extract comprising an effective amount of the compound trans-3-O-galloyol-3,3',5,5',7-pentahydroxyflavan.

10. The method of claim 9, in which the extract contains one or more compounds selected from the group consisting of quercitin-3'-O-glucoside, taxifolin-3'-O-glucoside, catechin and epicatechin.

11. The method of claim 10, in which the extract contains catechin and epicatechin in a ratio of approximately 1:1.

12. The method of claim 9, in which the extract is an extract of a plant of the genus *Elephantorrhiza*.

13. The method of claim 12, in which the plant is a plant of the species *E. elephantine* or *E. goetzi*.

14. The method of claim 12, in which the extract is an aqueous extract of the rhizomes of the plant.

15. The method of claim 9, in which the extract is a spray-dried or freeze-dried extract.

16. A method for treatment of benign prostatic hyperplasia (BPH) or a condition associated therewith comprising administering, to a human in need thereof, a pharmaceutical composition comprising an effective amount of the compounds selected from group consisting of trans-3-O-galloyol-3,3',5,5',7-pentahydroxyflavan, quercitin-3'-O-glucoside, taxifolin-3'-O-glucoside, catechin and epicatechin wherein the composition comprises a plant extract which contains the compounds, and wherein the plant extract is an extract of a plant of the genus *Elephantorrhiza*.

17. The method of claim 16, wherein the plant is a plant of the species *E. elephantine* or *E. goetzi*.

* * * * *